US008006693B2

(12) United States Patent
Vecellio-None et al.

(10) Patent No.: US 8,006,693 B2
(45) Date of Patent: Aug. 30, 2011

(54) AEROSOL TRANSFER DEVICE FOR MEDICAL AEROSOL GENERATORS OR MEDICAL AEROSOL GENERATOR SYSTEMS

(75) Inventors: Laurent Vecellio-None, Chambray les Tours (FR); Michel Massardier, Saint Etienne (FR); Gilles Chantrel, Saint Etienne (FR)

(73) Assignee: La Diffusion Technique Francaise, St. Etienne (FR)

( * ) Notice: Subject to any disclaimer, the term of this patent is extended or adjusted under 35 U.S.C. 154(b) by 905 days.

(21) Appl. No.: 11/314,625

(22) Filed: Dec. 21, 2005

(65) Prior Publication Data

US 2006/0137685 A1 Jun. 29, 2006

(30) Foreign Application Priority Data

Dec. 21, 2004 (FR) ...................................... 04 13784

(51) Int. Cl.
*A61M 16/00* (2006.01)
*A61M 15/00* (2006.01)
*A61M 11/00* (2006.01)

(52) U.S. Cl. ......... 128/203.15; 128/203.12; 128/200.24; 128/200.23; 128/200.14

(58) Field of Classification Search ............. 128/203.15, 128/203.12, 200.11–200.24; 239/102.1, 239/102.2, 338, 505, 335; 261/DIG. 65, 261/129, 154
See application file for complete search history.

(56) References Cited

U.S. PATENT DOCUMENTS

| | | | | | |
|---|---|---|---|---|---|
| 3,486,771 | A | * | 12/1969 | Conlin | 285/39 |
| 4,268,460 | A | * | 5/1981 | Boiarski et al. | 261/1 |
| 4,429,835 | A | * | 2/1984 | Brugger et al. | 239/338 |
| 4,534,343 | A | | 8/1985 | Nowacki et al. | 128/200.23 |
| 5,054,477 | A | * | 10/1991 | Terada et al. | 128/200.14 |
| 5,178,138 | A | * | 1/1993 | Walstrom et al. | 128/200.23 |
| 5,415,161 | A | * | 5/1995 | Ryder | 128/200.23 |
| 5,479,920 | A | * | 1/1996 | Piper et al. | 128/204.23 |
| 5,596,982 | A | * | 1/1997 | Blaha-Schnabel | 128/200.14 |
| 5,628,307 | A | * | 5/1997 | Clark et al. | 128/203.15 |
| 5,685,291 | A | * | 11/1997 | Marsh | 128/200.15 |
| 5,803,362 | A | * | 9/1998 | Fraccaroli | 239/102.2 |
| 6,070,573 | A | * | 6/2000 | Howe et al. | 128/200.14 |
| 6,336,455 | B1 | * | 1/2002 | Howlett | 128/203.15 |
| 6,340,023 | B2 | * | 1/2002 | Elkins | 128/200.21 |
| 6,363,932 | B1 | * | 4/2002 | Forchione et al. | 128/203.12 |

(Continued)

FOREIGN PATENT DOCUMENTS

GB 2 000 555 A 1/1979

(Continued)

*Primary Examiner* — Justine Yu
*Assistant Examiner* — Annette Dixon
(74) *Attorney, Agent, or Firm* — Heslin Rothenberg Farley & Mesiti P.C.

(57) ABSTRACT

An aerosol transfer device for medical aerosol generators comprises an elongate shaped hollow member, located in a vertical plane constituting an aerosol storage area. The member has a first opening allowing entry of outside air. The first opening is located on an upper or lower horizontal surface of the member to ensure vertical air entry. A second opening opposite said first opening allows escape of aerosol, and a third opening serves for spraying aerosol into the storage area in the vertical plane and in axial alignment with the air inlet opening. The member has a minimum height of 6 cm and allows dispersion of the sprayed aerosol without recycling aerosol deposited on the walls. The member is located between an aerosol generator source and a patient interface and does not include any valve on the aerosol path from the storage area to the patient.

17 Claims, 11 Drawing Sheets

U.S. PATENT DOCUMENTS

Figure 1:
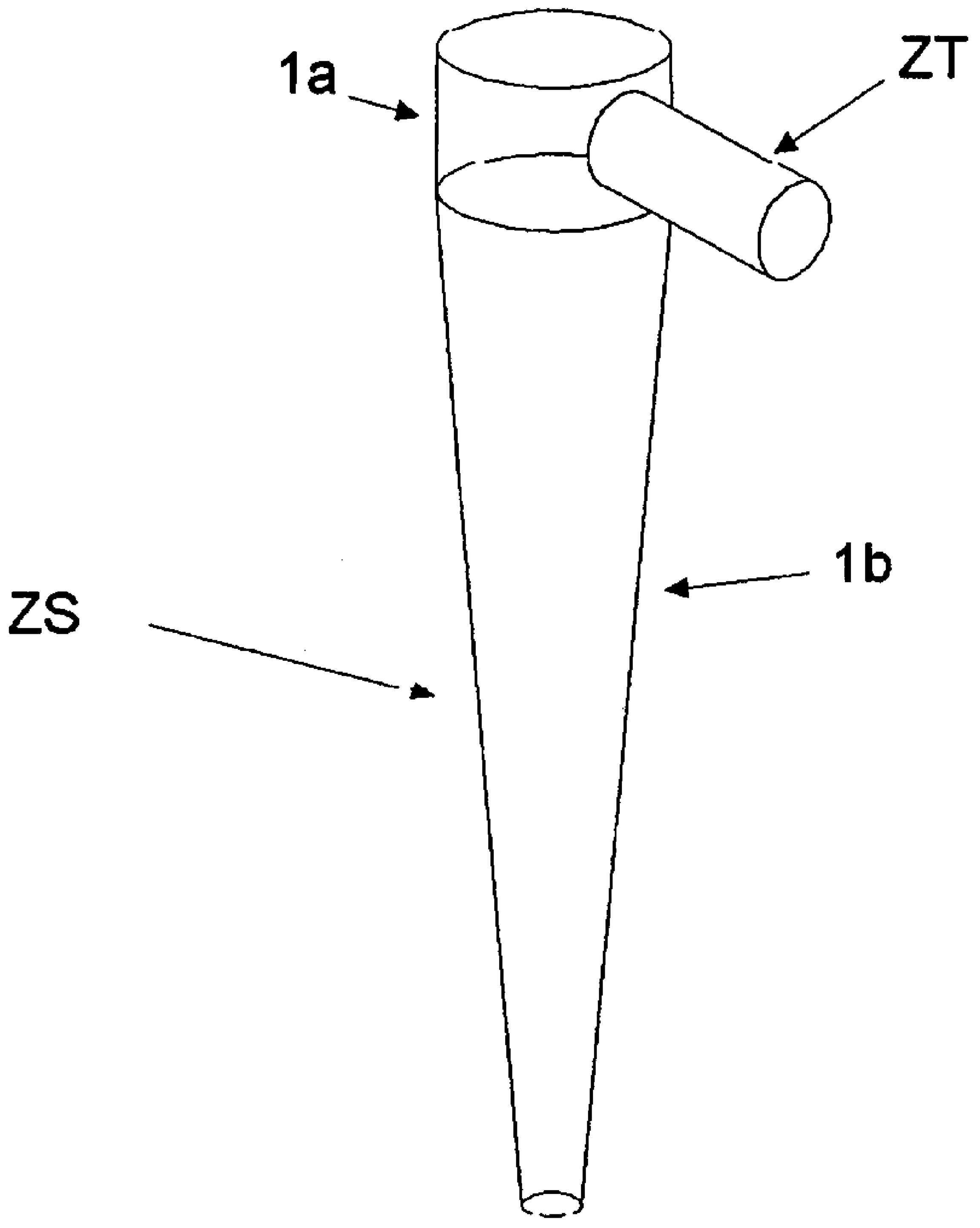

| | | | | |
|---|---|---|---|---|
| 6,412,481 | B1 * | 7/2002 | Bienvenu et al. | 128/200.21 |
| 6,932,082 | B2 * | 8/2005 | Stein | 128/200.22 |
| 6,962,151 | B1 * | 11/2005 | Knoch et al. | 128/200.14 |
| 2002/0104531 | A1 * | 8/2002 | Malone | 128/200.23 |
| 2003/0196654 | A1 * | 10/2003 | Stein | 128/200.23 |

FOREIGN PATENT DOCUMENTS

| | | | |
|---|---|---|---|
| WO | WO03/089036 | A1 | 10/2003 |

* cited by examiner

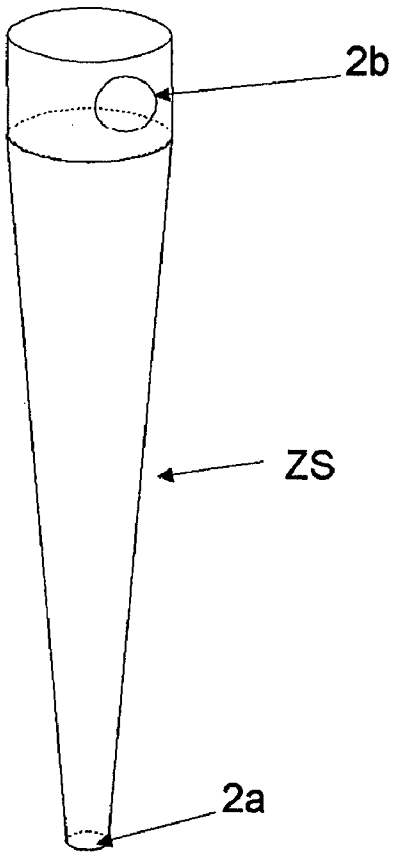
Figure 2.1
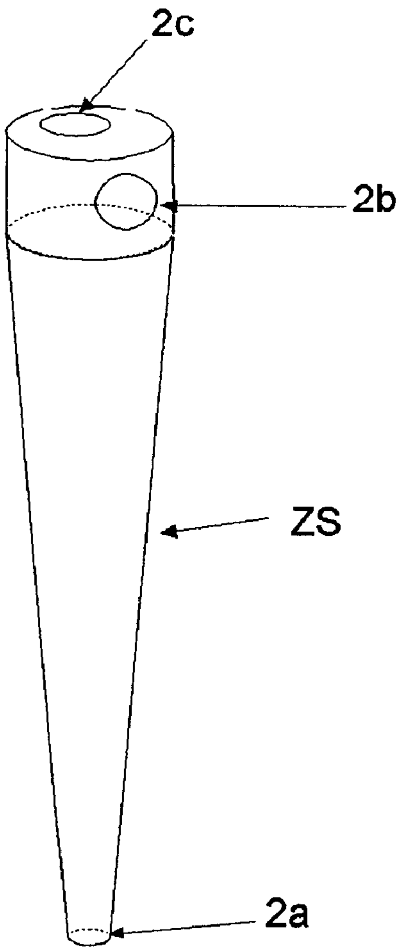
Figure 2.2

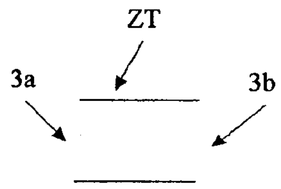
Figure 3.1
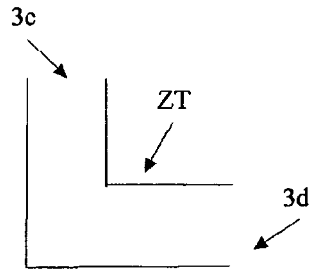
Figure 3.2
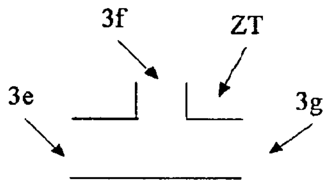
Figure 3.3

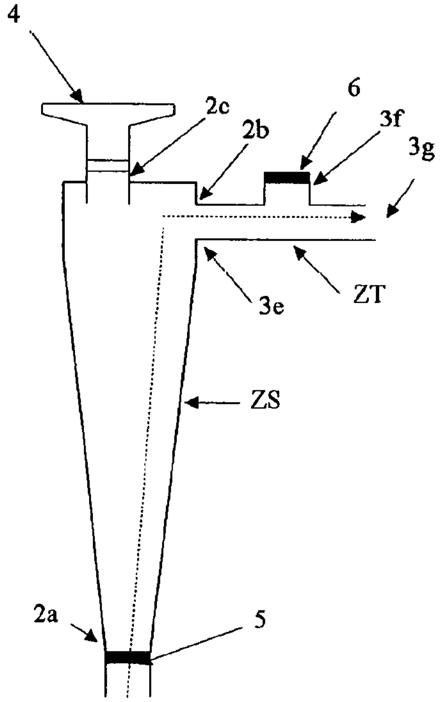
Figure 4.1
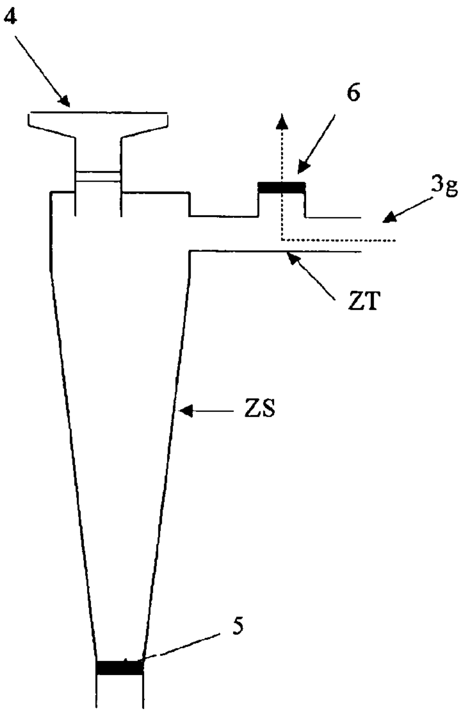
Figure 4.2

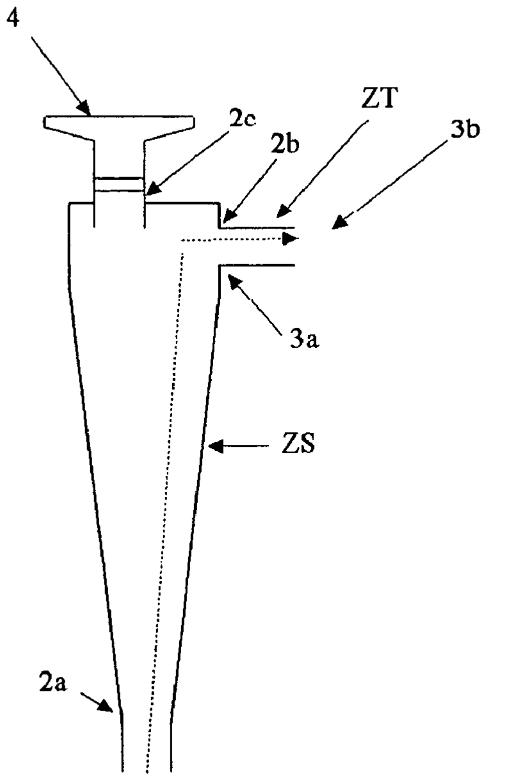
Figure 5.1
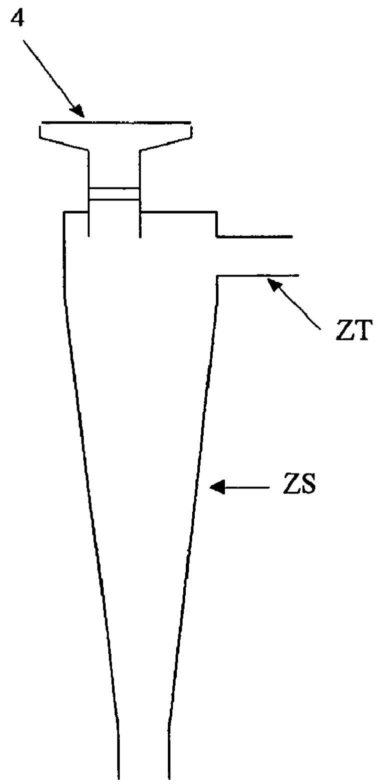
Figure 5.2

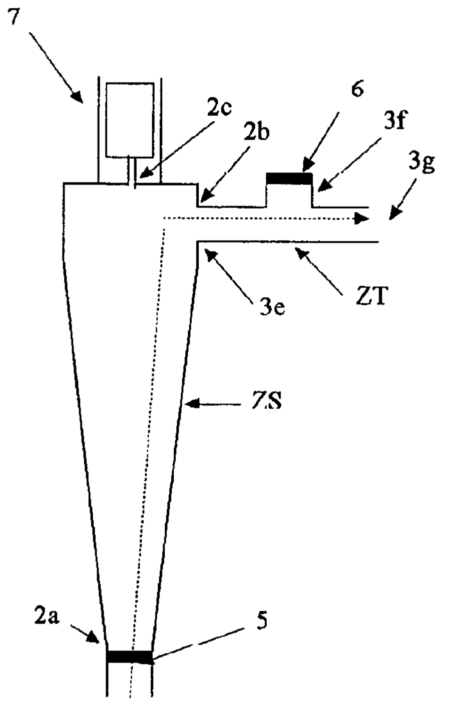
Figure 6.1
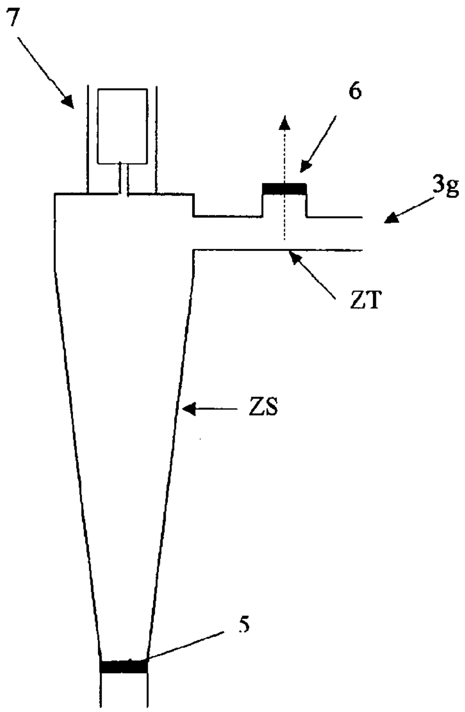
Figure 6.2

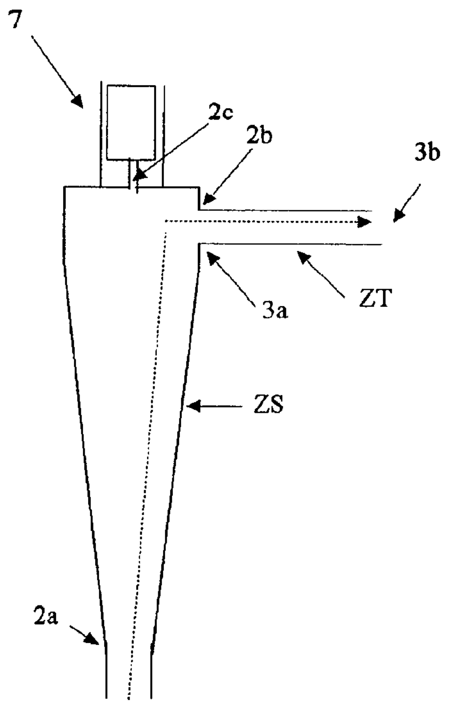
Figure 7.1
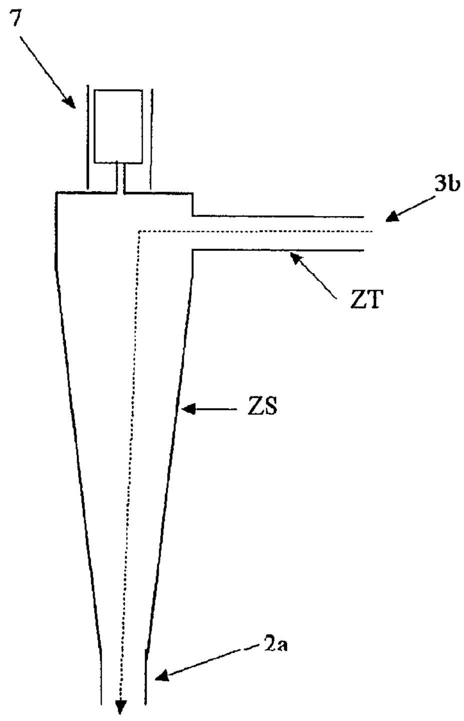
Figure 7.2

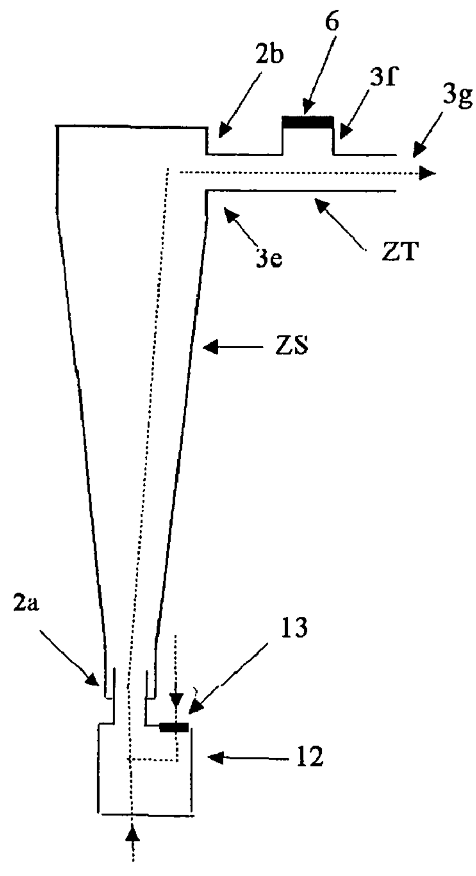
Figure 8.1
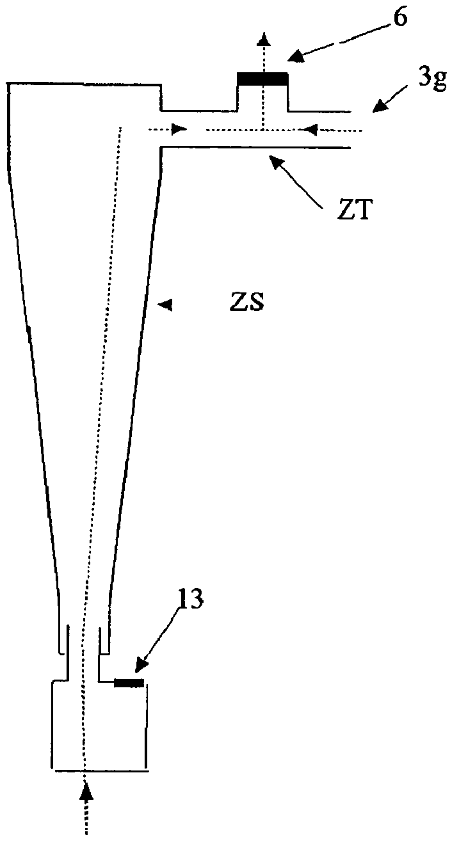
Figure 8.2

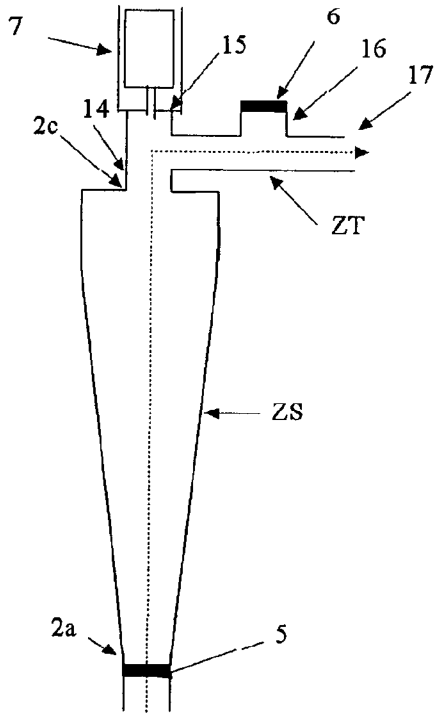
Figure 9.1
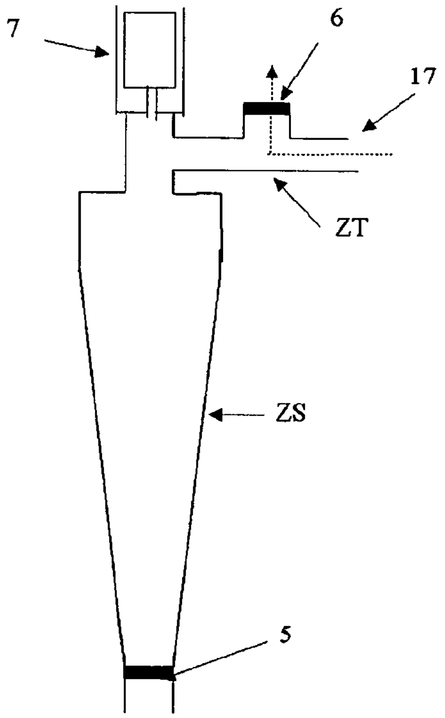
Figure 9.2

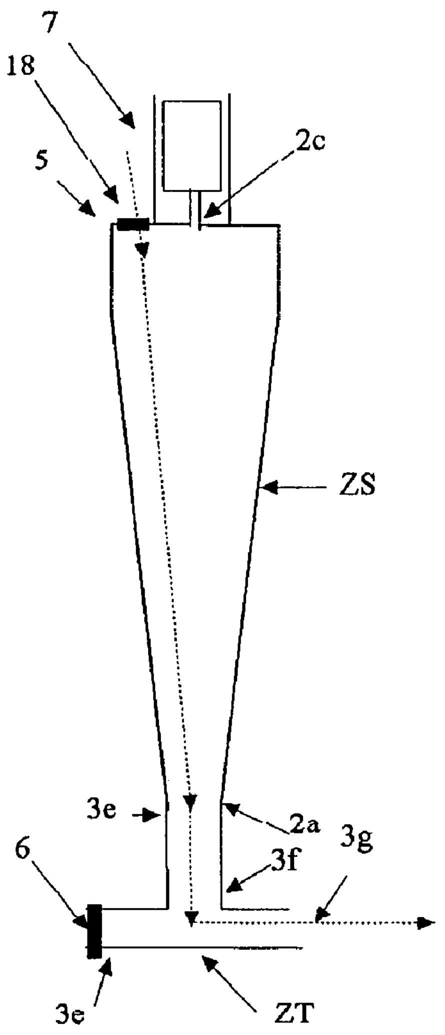
Figure 10.1
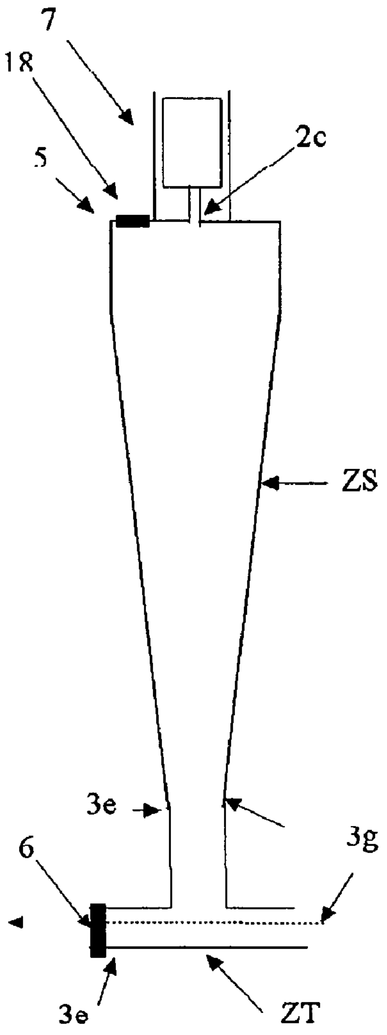
Figure 10.2

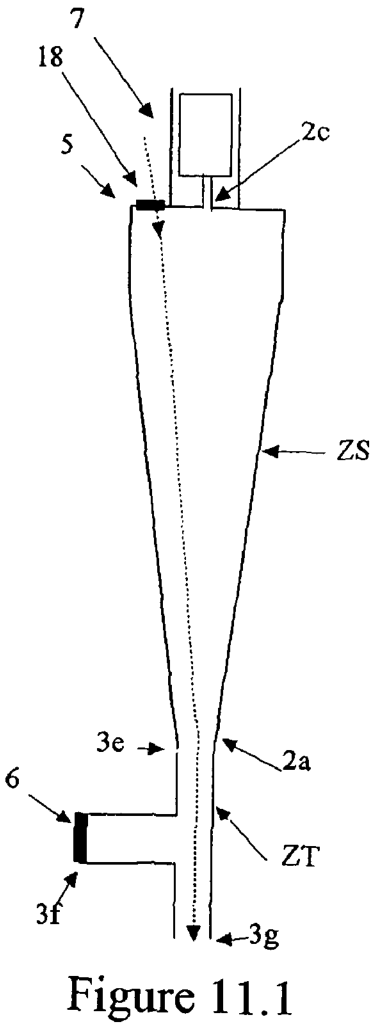
Figure 11.1
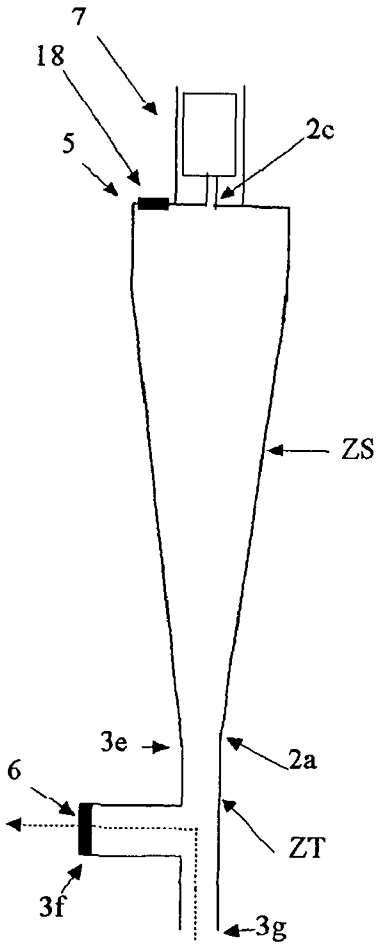
Figure 11.2

AEROSOL TRANSFER DEVICE FOR MEDICAL AEROSOL GENERATORS OR MEDICAL AEROSOL GENERATOR SYSTEMS

BACKGROUND OF THE INVENTION

The present invention relates to the technical field of medical aerosol generator systems.

The purpose of medical aerosol generator systems is to convert a medicated liquid or powder into aerosol form so that it can be administered to the airways of the respiratory tract.

There are various commercially available medical aerosol generator systems in the form of pneumatically controlled, ultrasonic and vibrating-membrane devices in particular, as well as pressurised canisters with a metering valve.

The Applicant is one of the leading firms that manufacture and market this type of device. Despite all the research efforts devoted to these devices (generators, nebulisers and pressurised canisters), the various published studies on this subject all agree and confirm that a large proportion of the dispensed aerosol is lost and wasted rather than being used for the desired therapeutic treatment. Authors and manufacturers alike estimate the proportion of aerosol that is actually used at approximately 25% (inhalable or available fraction). Losses are due to several parameters, including loss of the medication in the atmosphere when the patient exhales, the mass of medication lost in the nebuliser at the end of nebulisation and the mass lost during transfer of the aerosol. The design of devices with outlet vents is one explanation with the particles naturally escaping into the open air.

Inhaler chambers, for example in the case of pressurized canisters with a valve, are one means of limiting losses.

In this case, transfer of the aerosol essentially takes place in a container which is horizontal when the device is placed in/over the mouth so that the sprayed aerosol, the particle size distribution of which is highly variable and heterogeneous, partially fills the space in question. Thus, it is readily obvious that the larger sized particles tend to drop very quickly into the bottom of the horizontal container well before inhalation simply due to the effect of gravity. It is thus readily obvious that there is a fine layer of medicated particles that are not inhaled.

Some other devices, especially those with a vibrating membrane, make it possible to spray all the aerosol into a small vertical chamber but the lower part of this chamber forming a container is likely to receive medicated particles at high speed which causes impaction and therefore loss of medicated particles on the walls of the chamber. In any case and according to tests that have been performed, even in this type of device, active use of the dispensed aerosol is 25% of the volume introduced into the generator system on average.

According to the prior art as defined in the example in U.S. Pat. No. 5,596,982 and WO 03/089036, the aerosol generators use turbulence or vortex effects during transport of the aerosol and these are the cause of loss of aerosol particles. Obtaining this turbulence effect requires entry of air to take place in a plane that is perpendicular to the transport axis of the aerosol.

The objective of the invention is to reduce the loss of aerosols.

The Applicant's approach was therefore to rethink the problem of this partial use of the aerosol and to attempt to find a solution in order to improve the conditions for therapeutic treatment of patients.

Various possibilities were examined by reducing or eliminating the vent(s) or opening(s) on the nebuliser or introducing an additional blower system in order to increase the circulation of medicated aerosol through the horizontal transfer chamber to the area where the aerosol is inhaled by mouth.

In practice, it was impossible to adopt these solutions because they only partially solved the problem in question as they only improved the proportion of inhaled aerosol insignificantly.

BRIEF SUMMARY OF THE INVENTION

Faced with this situation, the Applicant then considered a different design concept for this type of device which, unexpectedly, improved the ability to hold the aerosol without it being deposited on the walls and increased the quantity of aerosol inhaled very significantly compared with the prior art. Initial trials and tests show that the proportion of aerosol inhaled is 40% to 90% compared with the abovementioned 25% figure.

According to a first aspect, the aerosol transfer device for medical aerosol generators is distinctive in that it comprises an elongate shaped hollow member or means located in a vertical plane constituting an aerosol storage area, said means being designed with a first opening allowing movement of air from outside the storage area into the latter and being located on the upper or lower horizontal surface of said means in order to ensure vertical entry of air into said means and in that it comprises a second opening opposite said first opening of said means allowing the escape of aerosol and in that it comprises an opening for spraying aerosol into the storage area in the vertical plane of the storage area and in axial alignment with the air inlet opening and in that said additional means that fulfils the storage function has a minimum height of 6 cm and allows dispersion of the sprayed aerosol throughout the space without recycling the aerosol deposited on the walls, said storage area being located between the aerosol generator source and the patient interface and allowing, by means of a transport area, aerosol transport to the patient and in that the device does not include any valve on the path the aerosol takes from the means that constitutes the storage area to the patient.

Thus, the device according to the invention is particularly advantageous because the combination of these features makes it possible to limit the loss of aerosol due to deposition on the walls. In fact, the particles which constitute medical aerosols have a diameter of the order of one micrometer in order to ensure they penetrate into and are deposited in the airways. Particles having diameters in this size range are affected by the force of gravity. The particles have a vertical downward trajectory due to the effect of gravity. Under these conditions, the particles fall due to the effect of their own weight (settling) until they encounter an obstacle and are deposited on it. The invention involves using a vertical space to store the aerosol in order to limit deposition of particles by settling. For example, by introducing an aerosol into the upper part of a vertical space intended to store the aerosol, the particles will take longer to be deposited on the bottom of the additional means than in the case of an equivalent space that extends in a horizontal plane. This additional means combined with the relative position of the air inlet and aerosol outlet openings therefore makes it possible to increase the quantity of aerosol stored between each inhalation and to limit its deposition on the walls. It also makes it possible to handle generation of an aerosol at a higher speed without losses on the walls. The space into which the aerosol is sprayed is sufficiently large for there to be enough time for the particles generated at high speed to be slowed down by air friction, thereby limiting their deposition when they impinge on the walls of the additional means. This additional means also makes it possible to concentrate the aerosol during the phase when the patient exhales, thus increasing the quantity of the active principle inhaled each time the subject breathes in, thereby increasing the flow rate of the system.

The invention therefore makes it possible to increase not only the efficiency of the aerosol generator system, but also its flow rate.

BRIEF DESCRIPTION OF THE DRAWING FIGURES

These aspects and others will become apparent from the following description.

FIG. 1 shows the basic principle of the invention in one embodiment of the aerosol transfer device, FIGS. 2.1 and 2.2 are schematic views of the configuration of the storage area (ZS).

FIGS. 3.1, 3.2 and 3.3 are schematic views showing configurations of the transport area (ZT) between the aerosol transfer device and the patient.

FIGS. 4.1 and 4.2 are views of the aerosol transfer device when it is used with a vibrating-membrane aerosol generator, especially for an ambulatory patient.

FIGS. 5.1 and 5.2 are views of the aerosol transfer device when it is used with an aerosol generator as part of mechanical ventilation of the patient.

FIGS. 6.1 and 6.2 are views of the aerosol transfer device when it is used with a metered-dose pressurised-canister aerosol generator in a first embodiment.

FIGS. 7.1 and 7.2 are views of the aerosol transfer device when it is used with a metered-dose pressurised-canister aerosol generator in a second embodiment.

FIGS. 8.1 and 8.2 are views of the aerosol transfer device when it is used with a pneumatic or ultrasonic aerosol generator with valves with an additional air inlet or an active venturi.

FIGS. 9.1 and 9.2 are views of the aerosol transfer device when it is used with a metered-dose pressurised-canister aerosol generator in another embodiment.

FIGS. 10.1 and 10.2 are views of the aerosol transfer device when it is used with a metered-dose pressurised-canister aerosol generator in another embodiment.

FIGS. 11.1 and 11.2 are views of the aerosol transfer device when it is used for a recumbent patient (patient confined to bed) with a metered-dose pressurised-canister aerosol generator.

DETAILED DESCRIPTION

Medical aerosol generator systems comprise the aerosol generator itself and an interface between the aerosol generator and the patient. The aerosol generator is the source from which the aerosol is generated. The patient/aerosol generator interface is used to transport the aerosol from the generator to the patient (e.g. mask, mouthpiece, nosepiece, mechanical ventilator circuit, intubation catheter, tracheal catheter, etc.). The invention relates to the intermediate area between the area where the aerosol is generated and the area where it is transported (ZT) to the patient. This intermediate area is referred to as the "storage area" (ZS) (FIG. 1).

This area can be physically represented by the aerosol transfer device. This aerosol transfer device, referred to in its entirety as (ZS) is intended to receive aerosol generated by the aerosol generator and then, via the patient/aerosol generator interface, to transport it out of the aerosol generator system. This aerosol transfer device can be an integral part of the aerosol generator system or be independent of it. Thus, the aerosol generator can be contained in the aerosol transfer device or be located on the interface.

This aerosol transfer device is shaped and located in a vertical plane. It has a minimum height of 6 cm. It can have a cross section of any shape and may comprise several different cross-sectional areas. It is vertical and long. Its upper part (1*a*) has a cylindrical neck and its bottom part (1*b*) has a bottomless tapered configuration (FIG. 1) (no flat surface at its lower end in order to limit aerosol deposition by settling).

In contrast to the nebulisation chambers of pneumatic or ultrasonic nebuliser type aerosol generators, the aerosol deposited on the walls of the transfer device is not recycled in liquid form so that it can be regenerated in aerosol form.

The aerosol transfer device described above has a minimum of two openings which link the space contained in the storage area (ZS) to the space outside the storage area (ZS).

In one of the configurations of the storage area, there can be two of these openings—FIG. 2.1—with openings (2*a*) and (2*b*) or three of these openings—FIG. 2.2—with openings (2*a*), (2*b*) and (2*c*).

At least one of these openings (2*b*) is intended to accommodate a patient/aerosol transfer device interface. The other opening (2*a*) or (2*c*) allows at least the movement of outside air through the device towards the patient/transfer device interface. Opening (2*c*) or (2*a*) allows the escape of aerosol. In the implementation according to the invention, opening (2*a*) allowing movement of air from outside the storage area into the storage area must be along the axis of the storage area, i.e. in a vertical plane. This opening (2*a*) is located on the upper or lower horizontal surface of the storage area. This makes it possible to limit turbulence and vortex effects which cause loss of particles. Opening (2*b*) allowing aerosol to escape from inside the storage area towards the patient is located at an opposite end of the storage area from the air entry opening so as to ensure complete aerosol transfer in the vertical plane of the storage area. Opening (2*c*) allowing aerosol to be sprayed by the generator is made in the upper and lower parts of the storage area in axial alignment with air inlet opening (2*a*) with vertical spraying of the aerosol into the storage area. The said openings may also often accommodate an aerosol generator. In the special case where the aerosol generator is located on said interface, there is no longer any connection to the aerosol generator. The other said openings may also accommodate valves and any other kinds of active or passive connections which are useful for the aerosol session.

Various configurations are shown. In one of the configurations, these openings can be located at the bottom of the aerosol transfer device as shown in FIG. 2.2, location (2*a*), at the top of the aerosol transfer device, location (2*c* ), or on the lateral surface of the aerosol transfer device, location (2*b*).

The interface between the aerosol transfer device and the patient contains at least two openings. One of the openings is connected to the aerosol transfer device. The other openings can be connected to the patient, to valves, aerosol generators and any other kinds of active or passive connections that are useful for the aerosol session. In one of the configurations of the interface between the aerosol transfer device and the patient, it can be a cylinder open at both ends—FIG. 3.1, openings (3*a*) and (3*b*)—an "L"-shaped part with a circular cross-section, open at both ends—FIG. 3.2, openings (3*c*) and (3*d*), a "T"-shaped part with a circular cross section and openings at three ends—FIG. 3.3, openings (3*e*), (3*f*) and (3*g*).

Various configurations of the aerosol transfer device can be envisaged on the basis of this principle, it being possible for the aerosol to be liquid or powder based depending on the configuration.

A first configuration of the transfer device is shown in FIGS. 4.1 and 4.2 and relates to the case where it is used with a vibrating-membrane aerosol generator, especially for an ambulatory patient. In this configuration, storage area (ZS) has three openings. A first opening (2*c* ) located at the top of the storage area (ZS) is intended to accommodate a vibrating-membrane nebuliser (4), a second opening (2*a*) located at the bottom is intended to accommodate a valve (5) and a third opening (2*b*) located on the lateral surface of the upper part is intended to accommodate the transport area (ZT) for transport to the patient. This is a T-shaped part with a circular cross section that has three openings (FIG. 4.1). Opening (3*e*) of area (ZT) is connected to opening (2*b*) of storage area (ZS) and opening (3*g*) of area (ZT) is connected to the patient. The third opening (3*f*) located at the top of area (ZT) (FIG. 4.1) is intended to accommodate a valve (6) (FIG. 4.1). In this configuration, during the inspiration phase (FIG. 4.1), valve (5) is opened and valve (6) is closed. Air that enters area (ZS) through valve (5) flows through storage area (ZS) from bottom to top in order to transport the aerosol to area (ZT). The aerosol is then transported from area (ZT) to the patient's mouth.

During the expiration phase (FIG. 4.2), valve (5) is closed and valve (6) is opened. The air exhaled by the patient does not flow through storage area (ZS) but is expelled from area (ZT) via valve (6). During the expiration phase, the aerosol continues to be produced and is stored in storage area (ZS) for the next inhalation.

A second configuration of the transfer device is shown (FIGS. 5.1 and 5.2) and relates to the case where it is used with an aerosol generator (vibrating-membrane generator in particular or metered-dose pressurised canister) as part of mechanical ventilation. In this configuration, storage area (ZS) has three openings. A first opening (2*c* ) located at the top of area (ZS) (FIG. 5.1) is intended to accommodate an aerosol generator ((4), a second opening (2*a*) located at the bottom is intended to be connected to the inspiration circuit of the mechanical ventilator system and a third opening (2*b*) located on the lateral surface of the upper part is intended to accommodate the transport area (ZT). The latter is a cylindrical part that has two openings. Opening (3*a*) of area (ZT) is connected to opening (2*b*) of storage area (ZS) and opening (3*b*) of area (ZT) is connected to the inspiration circuit of the mechanical ventilator system. In this configuration, the transfer device is interposed in the inspiration circuit of the mechanical ventilator system.

In this configuration, during the inspiration phase (FIG. 5.1), the air that enters area (ZS) through opening (2*a*) flows through storage area (ZS) from bottom to top in order to transport the aerosol to area (ZT). The aerosol is then transported from area (ZT) to the inspiration circuit of the mechanical ventilator system.

During the expiration phase (FIG. 5.2), the air flows via the expiration circuit of the mechanical ventilator system and therefore does not flow t through the aerosol transfer device. During this expiration phase, aerosol continues to be produced and is stored in storage area (ZS) for the next inhalation.

A third configuration of the transfer device is shown (FIGS. 6.1 and 6.2) and relates to the case where it is used with a metered-dose pressurised-canister aerosol generator for an ambulatory patient (generally referred to as a pressurised canister with a metering valve) which requires the use of a system with valves with area (ZT) located at the top of storage area (ZS). In this configuration, storage area (ZS) has three openings. A first opening (2*c* ) located at the top of storage area (ZS) (FIG. 6.1) is intended to accommodate the metered-dose pressurised canister (7), a second opening (2*a*) located at the bottom is intended to accommodate a valve (5) and a third opening (2*b*) located on the lateral surface of the upper part is intended to accommodate area (ZT). Area (ZT) is a T-shaped part with a circular cross section that has three openings (FIG. 6.1). Opening (3*e*) of area (ZT) is connected to opening (2*b*) of storage area (ZS) and opening (3*g*) of area (ZT) is connected to the patient. The third opening (3*f*) located at the top of area (ZT) is intended to accommodate a valve (6). In this configuration, during the inspiration phase (FIG. 6.1), valve (5) is opened and valve (6) is closed. Air that enters storage area (ZS) via valve (5) flows through storage area (ZS) from bottom to top in order to transport aerosol towards area (ZT). The aerosol is then transported from area (ZT) to the patient's mouth. During the expiration phase (FIG. 6.2), valve (5) is closed and valve (6) is opened. The air breathed out by the patient does not flow through area (ZS) but is expelled from area (ZT) via valve (6) and the aerosol remains stored in area (ZS) for the next inhalation.

A fourth configuration of the transfer device is shown (FIGS. 7.1 and 7.2) and relates to the case where it is used with a metered-dose pressurised-canister aerosol generator for ambulatory patients which does not require the use of a system with valves. In this configuration, area (ZS) has three openings. A first opening (2*c* ) located at the top of area (ZS) is intended to accommodate the metered-dose pressurised-canister (7), a second opening (2*a*) located at the bottom and a third opening (2*b*) located on the lateral surface of the upper part is intended to accommodate area (ZT). Area (ZT) is a cylindrical part that has two openings (FIG. 7.1). Opening (3*a*) of area (ZT) is connected to opening (2*b*) of area (ZS) and opening (3*b*) of area (ZT) is connected to the patient. During the inspiration phase, air that enters storage area (ZS) through opening (2*a*) flows through area (ZS) from bottom to top in order to transport aerosol to area (ZT). The aerosol is then transported from area (ZT) to the patient. Under these conditions, the patient will necessarily have to breathe in sufficiently deeply after the puff of aerosol has been produced in order to inhale all the aerosol stored in area (ZS). During the expiration phase (FIG. 7.2), the air breathed out by the patient flows through area (ZS) from top to bottom.

A fifth configuration of the transfer device is shown (FIGS. 8.1 and 8.2) and relates to the case where it is used with a pneumatic aerosol generator with a' valve with an active venturi or a, preferably ventilated, ultrasonic nebuliser with a valve. In this configuration, area (ZS) has two openings. A first opening (2*a*) at the bottom of area (ZS) is intended to accommodate the pneumatic or ultrasonic nebuliser (12) with a valve at (13) and a second opening (2*b*) located on the lateral surface of the upper part is intended to accommodate area (ZT). Area (ZT) is a T-shaped part with a circular cross section that has three openings. Opening (3*e*) of area (ZT) is connected to opening (2*b*) of area (ZS) and opening (3*g*) of area (ZT) is connected to the patient. The third opening located at the top of area (ZT) (3*f*) is intended to accommodate a valve (6). In this configuration, during the inspiration phase and, more precisely, if the patient's inspiration flow rate exceeds the air flow rate of the nebuliser, valve (13) is opened and valve (6) is closed. The air that enters area (ZS) via valve (13) and air from the nebuliser flow through area (ZS) from bottom to top in order to transport the aerosol to area (ZT). The aerosol is then transported from area (ZT) to the patient's mouth.

During the expiration phase (FIG. 8.2) and, more precisely, if the patient's inspiration flow rate is less than the air flow rate, valve (13) is closed and valve (6) is opened. The air breathed out by the patient does not flow through area (ZS) but is expelled from area (ZT) via valve (6). During the expiration phase, aerosol continues to be produced by air from the nebuliser. Air from the nebuliser containing aerosol particles flows through area (ZS) to area (ZT) and is then expelled from area (ZT) via valve (6). During transport within area (ZS), particles will settle in the flowing air due to their weight. The air directed towards area (ZT) will gradually contain fewer and fewer particles.

The aerosol stored in area (ZS) will be inhaled the next time the patient breathes in.

A sixth configuration of the transfer device is shown (FIGS. 9.1 and 9.2) and relates to the case where it is used with a metered-dose pressurised-canister aerosol generator for an ambulatory patient requiring the use of a system with valves with area (ZT) located at the top of area (ZS). In this configuration, area (ZS) has two openings. A first opening (2*c* ) located at the top of area (ZS) is intended to accommodate area (ZT), a second opening (2*a*) located at the bottom is intended to accommodate a valve (5). Area (ZT) is a part with a circular cross section that has four openings. Opening (14) of area (ZT) is connected to opening (2*c* ) of area (ZS), opening (15) of area (ZT) accommodates the aerosol generator (7), opening (16) of area (ZT) is intended to accommodate a valve (6) and opening (17) of area (ZT) is connected to the patient. In this configuration, during the inspiration phase, valve (5) is opened and valve (6) is closed. The air that enters area (ZS) via valve (5) flows through area (ZS) from bottom to top in order to transport aerosol to area (ZT). The aerosol is then transported from area (ZT) to the patient's mouth.

During the expiration phase (FIG. 9.2), valve (5) is closed and valve (6) is opened. The air breathed out by the patient does not flow through area (ZS) but is expelled from area (ZT) via valve (6), aerosol remains stored in area (ZS) for the next inhalation.

A seventh configuration of the transfer device is shown (FIGS. 10.1 and 10.2) and relates to the case where it is used with a metered-dose pressurised-canister aerosol generator for a patient in a seated or standing position requiring the use of a system with valves with area (ZT) located at the bottom of storage area (ZS). In this configuration, area (ZS) has three openings. A first opening (2*c* ) located at the top of area (ZS) (FIG. 12.1) is intended to accommodate the metered-dose pressurised-canister (7), a second opening (2*a*) located at the bottom is intended to accommodate area (ZT) and a third opening (18) located on the upper horizontal part is intended to accommodate a valve (5). Area (ZT) is a T-shaped part with a circular cross section which has three openings. Opening (3*e*) of area (ZT) is connected to opening (2*a*) of area (ZS) and opening (3*g*) of area (ZT) is connected to the patient. The third opening (3*f*) of area (ZT) is intended to accommodate a valve (6). In this configuration, during the inspiration phase (FIG. 10.1), valve (5) is opened and valve (6) is closed. The air that enters area (ZS) via valve (5) flows through area (ZS) from top to bottom in order to transport aerosol to area (ZT). The aerosol is then transported from area (ZT) to the patient's mouth.

During the expiration phase (FIG. 10.2), valve (5) is closed and valve (6) is opened. The air breathed out by the patient does not flow through area (ZS) but is expelled from area (ZT) via valve (6), aerosol remains stored in area (ZS) for the next inhalation.

An eighth configuration of the transfer device is shown (FIGS. 11.1 and 11.2) and relates to the case where it is used with a metered-dose pressurised-canister aerosol generator for a recumbent patient requiring the use of a system with valves with area (ZT) located at the bottom of storage area (ZS). In this configuration, area (ZS) has three openings. A first opening (2*c* ) located at the top of area (ZS) (FIG. 13.1) is intended to accommodate the metered-dose pressurized-canister (7), a second opening (2*a*) located at the bottom is intended to accommodate area (ZT) and a third opening (18) located on the upper horizontal part is intended to accommodate a valve (5). Area (ZT) is a T--shaped part with a circular cross section which has three openings.

Opening (3*e*) of area (ZT) is connected to opening (2*a*) of area (ZS) and opening (3*g*) of area (ZT) is connected to the patient. The third opening (3*f*) of area (ZT) is intended to accommodate a valve (6). In this configuration, during the inspiration phase (FIG. 11.1), valve (5) is opened and valve (6) is closed. The air that enters area (ZS) via valve (5) flows through area (ZS) from top to bottom in order to transport aerosol to area (ZT). The aerosol is then transported from area (ZT) to the patient's mouth.

During the expiration phase (FIG. 11.2), valve (5) is closed and valve (6) is opened. The air breathed out by the patient does not flow through area (ZS) but is expelled from area (ZT) via valve (6), aerosol remains stored in area (ZS) for the next inhalation.

In the above-mentioned configurations, the arrangement of the openings and valves may vary in terms of their position, the Figures being described and cited merely by way of example.

According to any of the configurations described above, the solution appears highly advantageous because tests that have been performed show that 40 to 90% of the aerosol dose, depending on the aerosol generator used, is inhaled by the patient, i.e. the proportion inhaled is of the order of three times that achieved by commercially available products.

The storage interface device according to the invention is easy to reuse and can be adapted to medical aerosol generators. It is also easy to clean.

Assessment of performance of the device in accordance with Standard NF-EN13544- 1.

European Standard EN13544-1 standardises an experimental method in order to determine the inhalable mass of aerosol produced by medical aerosol generators in order to assess medicated aerosol generators.

Measuring the inhalable mass involves filtering the aerosol produced during the inspiration phase under standardised patient ventilation conditions. This filtered mass is equivalent to the mass of aerosol delivered into the patient's mouth. The inhalable fraction is defined by the ratio of inhalable mass to the mass of medication fed into the aerosol generator.

In order to evaluate the effect of the device according to the invention on existing systems, we assessed the performance of aerosol generators without our device and then assessed the performance of the same aerosol generators with our device. A vibrating-membrane nebuliser, in particular (Aeroneb®, Aerogen, USA), was tested without the device according to the invention and then with the device according to the invention in configuration 1 (FIG. 4.1 and FIG. 4.2). A pressurised canister with a metering valve (Bricanyl®& metered-dose pressurised canister, Astra Zeneca, Sweden) was tested in one case with an inhalation chamber (Nebuhaler®, Astra Zeneca, Sweden) and in another case with our device in configuration 3 (FIG. 6.1 and FIG. 6.2). Pneumatic nebuliser NL9M® (La Diffusion Technique Francaise, Saint Etienne, France) was tested without the device according to the invention and then with the device according to the invention.

TABLE 1

Results of performance tests on medical aerosol generators in accordance with standard NF EN13544-1

| Aerosol generator | Inhalable fraction | Duration of session |
|---|---|---|
| NL9M ® | 25% | 4 min 30 sec |
| NL9M ® + device | 40% | 5 min |
| Aeroneb ® | 25% | 4 min 30 sec |
| Aeroneb ® + device | 91% | 4 min 30 sec |
| Bricanyl ® metered-dose canister + Nebuhaler ® | 14% | not applicable |
| Bricanyl ® metered-dose canister + device | 51% | not applicable |

The results demonstrate that the device according to the invention makes it possible, in every case, to increase the fraction of aerosol that can be inhaled by the patient. The device provides an increase in the performance of aerosol generators of 60% to 264% in terms of the inhalable aerosol mass. Because the device did not influence the duration of nebulisation, the results also demonstrate that the device makes it possible to increase the aerosol flow rate administered to the patient. In the case of the Bricanyl® metered-dose pressurised-canister aerosol generator, there is no session duration because the dose was delivered instantly (several tenths of a second).

The invention claimed is:

1. An aerosol transfer device for a medical aerosol generator comprising an elongate shaped hollow member oriented in a vertical direction during use and constituting an aerosol storage area, said elongate shaped hollow member having a first air entry opening for introducing outside air from outside the storage area into the storage area during an inhalation phase of operation of the device, and said air entry opening being located on an upper or lower horizontal surface of said elongate shaped hollow member in order to ensure vertical entry of the outside air into said elongate shaped hollow member, a second opening and a third opening located near an opposite end of said elongate shaped hollow member from said first opening, said second opening serving to eject aerosol from said elongate shaped hollow member, said third opening serving for vertically spraying aerosol into the storage area, said elongate shaped hollow member having a minimum height of 6 cm and wherein an upper part of the elongate shaped hollow member has a cylindrical neck and a lower part has a bottomless tapered configuration in order to enhance the transport of aerosol within the elongate shaped follow member allowing dispersion without recycling aerosol deposited on walls of said elongate shaped hollow member, said storage area being located between an aerosol generator source and a patient interface and allowing, via a transport area, aerosol transport to a patient, and wherein the device does not include any valve in a path the aerosol takes from the elongate shaped hollow member that constitutes the storage area to the patient, and wherein, during inhalation, the outside air is vertically introduced into said storage area through said first opening and aerosol travels vertically in said storage area and is ejected through said second opening.

2. The device as claimed in claim 1, in combination with the transport area, wherein the transport area comprises a cylinder that is open at both ends.

3. The device as claimed in claim 1, in combination with the transport area, wherein the transport area comprises an L-shaped part with a circular cross section that is open at both ends.

4. The device as claimed in claim 1, in combination with the transport area, wherein the transport area comprises a T-shaped part with a circular cross section and openings at three ends.

5. A device as claimed in claim 1, wherein the vertical travel of aerosol in said storage area is substantially turbulence free.

6. A device as claimed in claim 1, wherein the third opening is coaxial with the first opening.

7. A device as claimed in claim 1, wherein, during exhalation, air exhaled by the patient is expelled via a valve from the transport area and no exhaled air flows through the storage area.

8. The device as claimed in claim 1, wherein an upper part of the elongate shaped means has a greater cross-sectional area than a lower part of the elongate shaped means, and the air entry opening is located in said lower part.

9. The device as claimed in claim 1, further comprising means for maintaining the elongate shaped means oriented in the vertical direction during use.

10. The device as claimed in claim 9, wherein the means for maintaining the elongate shaped means oriented in a vertical direction during use comprises a mounting of the elongate shaped means to a patient interface dependent upon whether the patient is recumbent or ambulatory.

11. The device as claimed in claim 1, wherein the proportion of aerosol available for inhalation is between 40% and 90%.

12. An apparatus for administering an aerosol comprising the aerosol transfer device as claimed in claim 1 and a vibrating-membrane aerosol generator.

13. An apparatus for administering an aerosol comprising the aerosol transfer device as claimed in claim 1 and an aerosol generator comprising a pneumatic nebuliser.

14. An apparatus for administering an aerosol comprising the aerosol transfer device as claimed in claim 1 and an aerosol generator comprising an ultrasonic nebuliser.

15. An apparatus for administering an aerosol comprising the aerosol transfer device as claimed in claim 1 and an aerosol generator comprising a pressurized canister fitted with a metering valve.

16. A method for providing an enhanced proportion of medical aerosol to a patient, comprising:

connecting the aerosol transfer device of claim 1 between an aerosol generator source and a patient interface;

maintaining the elongate shaped hollow member oriented in the vertical direction during use;

vertically introducing outside air through the first opening and vertically spraying aerosol from the source through the third opening into the storage area; and transporting aerosol ejected from the elongate shaped hollow member through the second opening to the patient.

17. An aerosol transfer device for a medical aerosol generator comprising an elongate shaped hollow member oriented in a vertical direction during use and constituting an aerosol storage area, said elongate shaped hollow member having a first air entry opening for introducing outside air from outside the storage area into the storage area during an inhalation phase of operation of the device, and said air entry opening being located on an upper or lower horizontal surface of said elongate shaped hollow member in order to ensure vertical entry of the outside air into said elongate shaped hollow member, a second opening located near an opposite end of said elongate shaped hollow member from said first opening , said second opening serving to eject aerosol from said elongate shaped hollow member, and a third opening for vertically spraying aerosol into the storage area, said elongate shaped hollow member having a minimum height of 6 cm and wherein an upper part of the elongate shaped hollow member has a cylindrical neck and a lower part has a bottomless tapered configuration in order to enhance the transport of aerosol within the elongate shaped follow member allowing dispersion storage area without recycling aerosol deposited on walls of said elongate shaped hollow member, said storage area being located between an aerosol generator source and a patient interface and allowing, via a transport area, aerosol transport to a patient, and wherein the device does not include any valve in a path the aerosol takes from the elongate shaped hollow member that constitutes the storage area to the patient, and wherein, during inhalation, the outside air is vertically introduced into said storage area through said first opening and aerosol travels vertically in said storage area and is ejected through said second opening, and, during exhalation, air exhaled by the patient is expelled via a valve from the transport area and no exhaled air flows through the storage area.

* * * * *

UNITED STATES PATENT AND TRADEMARK OFFICE

CERTIFICATE OF CORRECTION

PATENT NO. : 8,006,693 B2
APPLICATION NO. : 11/314625
DATED : August 30, 2011
INVENTOR(S) : Vecellio-None et al.

It is certified that error appears in the above-identified patent and that said Letters Patent is hereby corrected as shown below:

Claim 1, column 9, line 49, delete “follow” and instead insert --hollow--

Claim 1, column 9, line 50, after “dispersion” insert --of sprayed aerosol throughout the aerosol storage area--

Claim 17, column 11, line 5, delete “follow” and instead insert --hollow--

Claim 17, column 11, line 6, after “dispersion” add --of sprayed aerosol throughout the aerosol--

Signed and Sealed this
Eighteenth Day of October, 2011

David J. Kappos
*Director of the United States Patent and Trademark Office*